United States Patent
Chou et al.

(10) Patent No.: US 8,582,111 B2
(45) Date of Patent: Nov. 12, 2013

(54) OPTICAL COHERENCE TOMOGRAPHY APPARATUS AND OPERATING METHOD THEREOF

(75) Inventors: Chung-Cheng Chou, Taoyuan County (TW); William Wang, Taoyuan (TW)

(73) Assignee: Crystalvue Medical Corporation, Taoyuan (TW)

( * ) Notice: Subject to any disclaimer, the term of this patent is extended or adjusted under 35 U.S.C. 154(b) by 285 days.

(21) Appl. No.: 12/960,235

(22) Filed: Dec. 3, 2010

(65) Prior Publication Data
US 2011/0134435 A1   Jun. 9, 2011

(30) Foreign Application Priority Data
Dec. 4, 2009 (TW) .................... 98141537 A

(51) Int. Cl.
*G01B 11/02* (2006.01)
(52) U.S. Cl.
USPC ........................................................ 356/497
(58) Field of Classification Search
USPC ................ 356/479, 497, 511, 477, 483, 450
See application file for complete search history.

(56) References Cited

U.S. PATENT DOCUMENTS

| | | | | |
|---|---|---|---|---|
| 6,069,698 A | * | 5/2000 | Ozawa et al. | 356/511 |
| 6,509,961 B1 | * | 1/2003 | Schroeder | 356/73.1 |
| 2003/0016901 A1 | * | 1/2003 | Cormack | 385/15 |

\* cited by examiner

*Primary Examiner* — Gregory J Toatley, Jr.
*Assistant Examiner* — Rufus Phillips
(74) *Attorney, Agent, or Firm* — Muncy, Geissler, Olds & Lowe, PLLC

(57) ABSTRACT

An optical coherence tomography apparatus includes a light source, a light coupling module, and an optical path difference generating module. The light source emits a coherent light. The light coupling module divides the coherent light into a first incident light and a second incident light. The first incident light is emitted to an item to be inspected and a first reflected light is generated. The second incident light is emitted to the optical path difference generating module, a second reflected light is generated according to the second incident light by the optical path difference generating module through changing the transparent/reflection properties of at least one optical devices of the optical path difference generating module, so that there is a optical path difference between the first reflected light and the second reflected light.

8 Claims, 7 Drawing Sheets

OPTICAL COHERENCE TOMOGRAPHY APPARATUS AND OPERATING METHOD THEREOF

BACKGROUND OF THE INVENTION

1. Field of the Invention

The invention relates to optical inspection, in particular, to an optical coherence tomography (OCT) apparatus and an OCT apparatus operating method capable of providing an optical path difference and a light frequency changing effect.

2. Description of the Prior Art

In recent years, with the development of the optical inspection technology, an optical image scanning technology provides a non-invasion way to know the structure and composition of the item to be inspected, and it is widely used in medical diagnosis due to its features of rapidity and non-invasion. When a light is emitted into the structure of the item, the absorption characteristic and scattering characteristic of the light will be changed in the medium with different depths. The optical image scanning technology is to use different optical methods to obtain the information carried by the scattered photon in the structure of the item to obtain a high-resolution image.

In general, a medical imaging technology is to measure the physical characteristic changes generated after a physical field source is provided to a biological tissue, and convert them into visual images to help the doctor to judge whether the structure of the biological tissue is formal and dynamically make a functional evaluation, so that the rapid and correct diagnosis and treatment can be provided to enhance medical quality. And, the medical imaging technology is currently developed toward the directions of using non-ionizing energy field source, measuring the image in the non-invasion way, having high space resolution and high contrast resolution, and real-time imaging capability.

Among the known medical imaging technologies, a medical imaging technology called "optical coherence tomography" (OCT) is developed rapidly and used in many application regions. The OCT technology is also called "optical biopsy" and uses a low coherence light source and a measurement structure of changing optical path difference interferometer to measure the coherence characteristic of the back-scattering light field strength of the biological tissue, and further to form a 2-D image or 3-D image. Therefore, the OCT technology can meet the development directions of the medical imaging technology, and many research groups pay attentions to it, so that the OCT technology is developed rapidly and used in many application regions.

In practical applications, since the OCT technology has the advantages of high resolution, high sensitivity, non-ionizing energy field source, and low cost, and the OCT technology can measure the cross-sectional structure of the tissue in the item and flowing velocity distribution diagram to provide the micro-meter level high resolution image. Therefore, the OCT technology has great help to diagnose the disease of the tissue and position the structure of the cell, for example, the retina of the eyeball.

Please refer to FIG. 1. FIG. 1 illustrates a schematic diagram of a conventional OCT apparatus. As shown in FIG. 1, the OCT apparatus uses the Michelson interferometer to divide the coherent light emitted from the coherent light source 10 into two light beams via the light splitter 12: one light is emitted to the reference end 16c and reflected by the reference end 16c; the other light is emitted to the item to be inspected T and reflected by the item to be inspected T. These two reflected lights will be passed through the light splitter 12 and transmitted to the light sensor 17, and the computer 18 will calculate the optical path difference between these two reflected lights and obtain a vertical cross-sectional optical data related to the item to be inspected T according to the optical path difference. In fact, the light sensor 17 can be a spectrometer, optical lens set, or any other devices having the light sensing function.

In addition, please refer to FIG. 2. FIG. 2 illustrates a schematic diagram of the basic structure of the OCT apparatus of FIG. 1. In order to generate the optical path difference between the reference end 14 and the item to be inspected 16, the OCT apparatus 1 needs some complicated optical devices, for example, an optical grating system, a rotation mechanism, and a light source 10 having changeable frequency, and also needs a shifting or rotating mechanical structure to generate the optical path difference. FIG. 2 also shows that the conventional OCT apparatus 1 changes the position of the reflection mirror 14 (moving parallel to the z-direction of FIG. 2 or rotating) to obtain different optical path differences, and obtain the sensing result of the item to be inspected 16 in the direction of depth (the z-direction of FIG. 2) through the Michelson interference effect.

No matter the OCT apparatus in FIG. 1 or the OCT apparatus in FIG. 2, a shifting or rotating mechanical structure will be necessary to generate the optical path difference, not only the cost of the OCT apparatus will be increased, but also the structure of the OCT apparatus will become complicated, and its volume will also become huger. Therefore, the invention provides an OCT apparatus and an operating method thereof to solve the above-mentioned problems.

SUMMARY OF THE INVENTION

A first embodiment of the invention is an OCT apparatus. In this embodiment, the OCT apparatus includes a light source, a light coupling module, and an optical path difference generating module. The optical path difference generating module includes at least one optical device. The light source is used for emitting a coherent light. The light coupling module is used for dividing the coherent light into a first incident light and a second incident light. The first incident light is emitted to an item to be inspected and a first reflected light is generated. When the second incident light is emitted to the optical path difference generating module, the optical path difference generating module will change the transparent/reflection properties of the at least one optical device to generate a second reflected light according to the second incident light to generate an optical path difference between the first reflected light and the second reflected light.

In practical applications, the at least one optical device can be a plurality of liquid crystal units arranged in a multi-layer form, a multi-layer electro-chromic material, a multi-layer electro-wetting structure unit, a plurality of light guide units, or a plurality of light switch units, the optical path difference generating module changes the transparent/reflection properties of the at least one optical device to generate the optical path difference without any mechanical structure.

A second embodiment of the invention is an OCT apparatus operating method. In this embodiment, the OCT apparatus includes a light source, a light coupling module, and an optical path difference generating module. The optical path difference generating module includes at least one optical device. The method includes the steps of: (a) the light source emitting a coherent light; (b) the light coupling module dividing the coherent light into a first incident light and a second incident light; (c) emitting the first incident light to an item to be inspected to generate a first reflected light; (d) when the second incident light is emitted to the optical path difference generating module, the optical path difference generating module changing the transparent/reflection properties of the at least one optical device to generate a second reflected light according to the second incident light to generate an optical path difference between the first reflected light and the second reflected light.

In practical applications, the at least one optical device can be a plurality of liquid crystal units arranged in a multi-layer form, a multi-layer electro-chromic material, a multi-layer electro-wetting structure unit, a plurality of light guide units, or a plurality of light switch units, the method changes the transparent/reflection properties of the at least one optical device to generate the optical path difference without any mechanical structure.

Compared to the prior arts, the OCT apparatus and its operating method of the invention is to change the transparent/reflection properties of its optical devices (for example, the liquid crystal unit, the electro-chromic material, the electro-wetting structure unit, the light guide unit, and the light switch unit) to generate an optical path difference, thus, the drawbacks of the conventional OCT apparatus that the complicated optical devices and the shifting/rotating mechanical structure are necessary to generate the optical path difference can be avoided. Therefore, the structure of the OCT apparatus can be largely simplified, and its manufacturing cost can be also reduced, even the effect of changing light frequencies can be provided according to the relationships between the color lights and the wavelengths, so that it has great market potential.

The advantage and spirit of the invention may be understood by the following recitations together with the appended drawings.

BRIEF DESCRIPTION OF THE APPENDED DRAWINGS

DETAILED DESCRIPTION OF THE INVENTION

Figure 1:
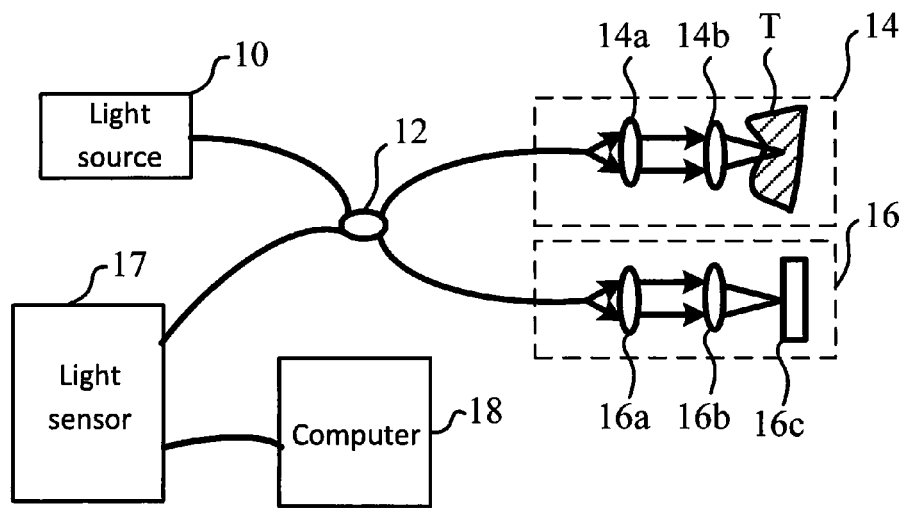
FIG. 1 illustrates a schematic diagram of the conventional OCT apparatus.
Figure 2:
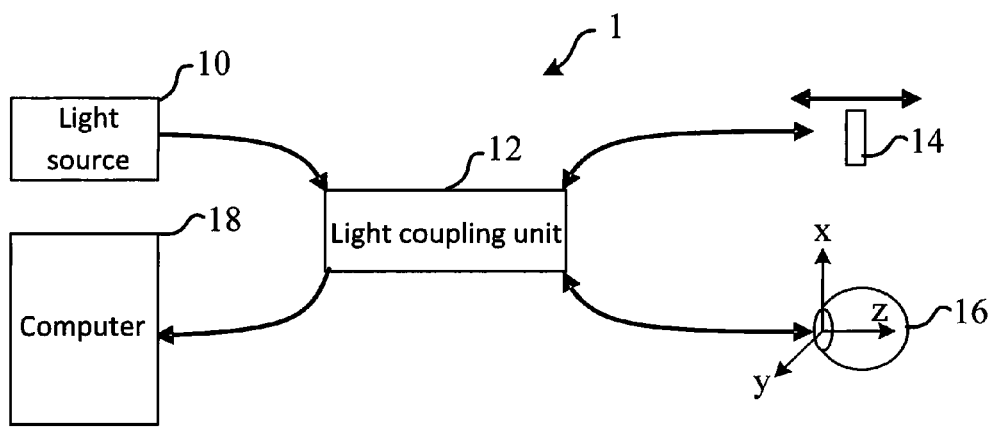
FIG. 2 illustrates a schematic diagram of the basic structure of the OCT apparatus of FIG. 1.
Figure 3:
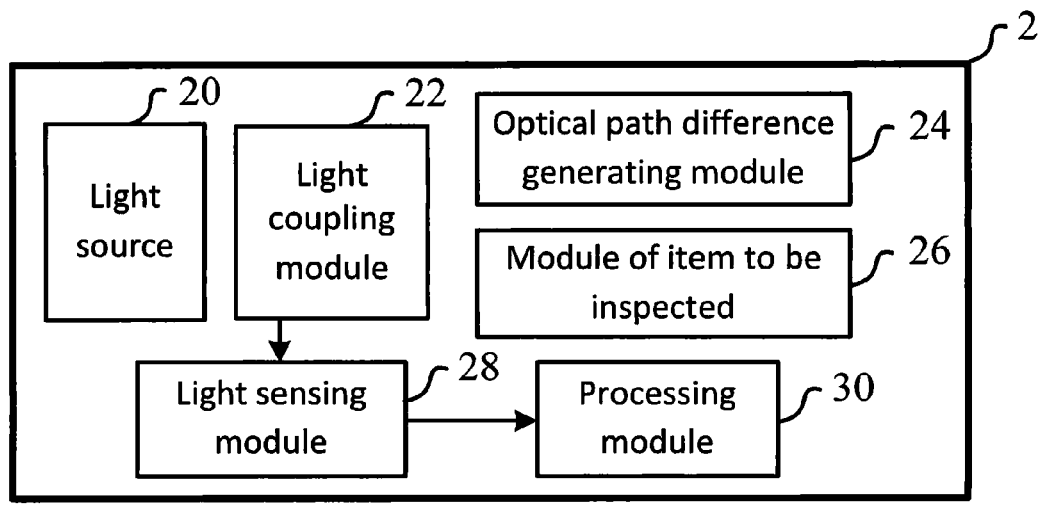
FIG. 3 illustrates a functional block diagram of the OCT apparatus of the first embodiment in the invention.

A first embodiment of the invention is an optical coherence tomography (OCT) apparatus. In this embodiment, the OCT apparatus is used to perform an inspection on an item to be inspected to obtain the vertical cross-sectional optical data related to the item to be inspected. Please refer to FIG. 3. FIG. 3 illustrates a functional block diagram of the OCT apparatus of the first embodiment in the invention.

As shown in FIG. 3, the OCT apparatus 2 includes a light source 20, a light coupling module 22, an optical path difference generating module 24, a module of item to be inspected 26, a light sensing module 28, and a processing module 30. Wherein, the light coupling module 22 is coupled to the light sensing module 28; the light sensing module 28 is coupled to the processing module 30. In addition, the light source 20 is a coherent light source; the light coupling module 22 is a light splitter or any other devices having the light splitting function; the module of item to be inspected 26 is used to dispose the item to be inspected; the optical path difference generating module 24 includes at least one optical device, and the at least one optical device can be a plurality of liquid crystal units arranged in a multi-layer form, a multi-layer electro-chromic material, a multi-layer electro-wetting structure unit, a plurality of light guide units, or a plurality of light switch units, there is no specific limitations.

In this embodiment, the light source 20 is used to emit a coherent light. The light coupling module 22 is used for dividing the coherent light emitted from the light source 20 into a first incident light and a second incident light, wherein the first incident light is emitted to the module of item to be inspected 26 and the second incident light is emitted to the optical path difference generating module 24. When the first incident light is emitted to the item to be inspected of the module of item to be inspected 26, the item to be inspected will reflect the first incident light to generate a first reflected light. When the second incident light is emitted to the optical path difference generating module 24, the optical path difference generating module 24 will change the transparent/reflection properties of the at least one optical device to generate a second reflected light according to the second incident light to generate an optical path difference between the first reflected light and the second reflected light.

It should be noticed that when the optical path difference generating module 24 changes the transparent/reflection properties of the at least one optical device to generate the optical path difference, since the transparent/reflection degree of each optical device to the second incident light can be measured in advance, that is to say, the transparent/reflection degree of each optical device to the second incident light is the information that is already known, and the position of each optical device of the optical path difference generating module 24 is also known.

Therefore, no matter how the optical path difference generating module 24 changes the transparent/reflection properties of the at least one optical device, the optical path difference generated by the optical path difference generating module 24 is also known, and the corresponding relationships between the transparent/reflection property of each optical device and different optical path differences can be recorded in a look-up table for the following comparison, but it is not limited by this case.

Compared to the prior arts, since the position of each optical device in the optical path difference generating module 24 of the invention is fixed and already known, it is unnecessary to use complicated mechanical way to move the optical device to change the optical path difference, so that the structure of the OCT apparatus can be simplified and the volume of the OCT apparatus can be reduced.

Figure 4A:
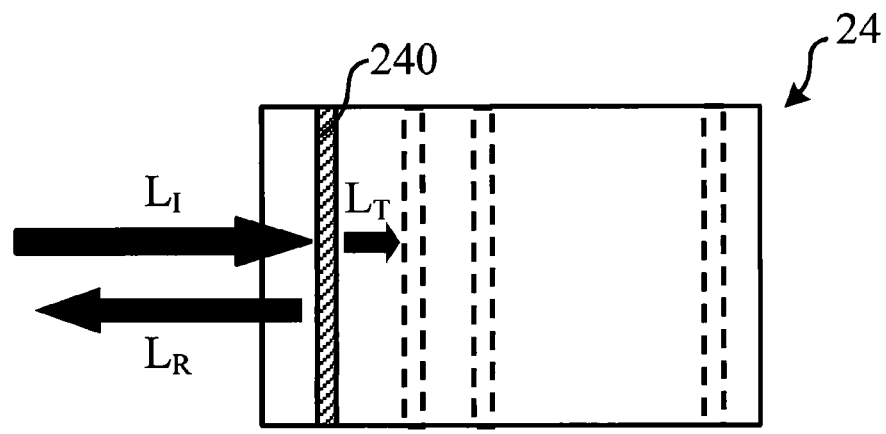
FIG. 4A illustrates a schematic diagram of the optical path difference generating module including a plurality of liquid crystal unit layers arranged in a multi-layer form.

Because the main feature of the invention distinguishable from the prior art is the optical path difference generating module 24, therefore, the different structures of the optical path difference generating module 24 and the different reflection conditions of the optical path difference generating module 24 reflecting the second incident light will be discussed as follows. Please refer to FIG. 4A. FIG. 4A illustrates a schematic diagram of the optical path difference generating module 24 including a plurality of liquid crystal unit layers 240 arranged in a multi-layer form. As shown in FIG. 4A, because the liquid crystal unit layers 240 are arranged vertical to the second incident light $L_I$, therefore, when the second incident light $L_I$ is emitted to the optical path difference generating module 24, most of the second incident light $L_I$ will be reflected by the liquid crystal unit layers 240 to generate a second reflected light $L_R$, and only a small part of the second incident light $L_I$ will pass through the liquid crystal unit layers 240 to generate a second transparent light $L_T$.

Figures 4B, 4C:
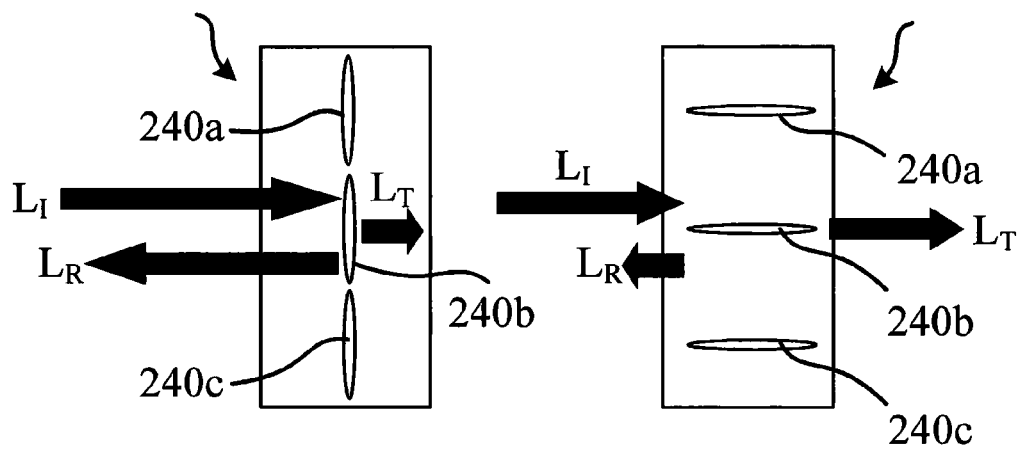
FIG. 4B illustrates a schematic diagram of the liquid crystal unit moving parallel to the second incident light to generate the light path difference.
FIG. 4C illustrates a schematic diagram of the liquid crystal unit rotating to generate the light path difference.

Next, please further refer to FIG. 4B. FIG. 4B illustrates a schematic diagram of the liquid crystal unit layer 240 including the liquid crystal units 240a~240c arranged vertical to the second incident light $L_I$. As shown in FIG. 4B, since the liquid crystal units 240a~240c in the liquid crystal unit layer 240 are all arranged vertical to the second incident light $L_I$, therefore, most of the second incident light $L_I$ will be reflected by the liquid crystal unit layers 240 to generate a second reflected light $L_R$, and only a small part of the second incident light $L_I$ will pass through the liquid crystal unit layers 240 to generate a second transparent light $L_T$.

On the contrary, please refer to FIG. 4C. FIG. 4C illustrates a schematic diagram of the liquid crystal unit layer 240 including the liquid crystal units 240a-240c arranged parallel to the second incident light $L_I$. As shown in FIG. 4C, since the liquid crystal units 240a-240c in the liquid crystal unit layer 240 are all arranged parallel to the second incident light $L_I$, therefore, most of the second incident light $L_I$ will pass through the liquid crystal unit layers 240 to generate a second transparent light $L_T$, and only a small part of the second incident light $L_I$ will be reflected by the liquid crystal unit layers 240 to generate a second reflected light $L_R$.

It should be noticed that no matter in the above-mentioned embodiments of FIG. 4A~FIG. 4C, or all the following embodiments, when the incident light is emitted to different optical path difference generating modules, only a part of the incident light can pass through, and the other part of the incident light will be reflected. Therefore, it will not be mentioned again in the following embodiments.

Figure 4D:
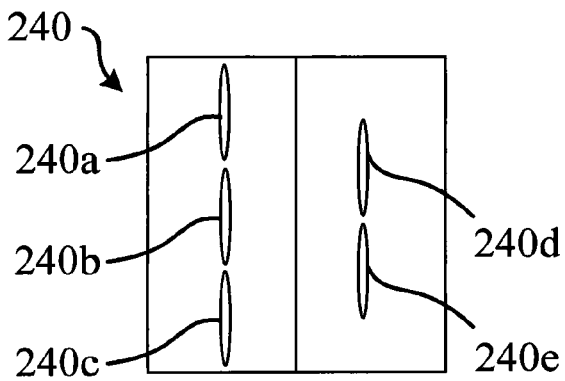
FIG. 4D illustrates a schematic diagram of the liquid crystal unit layer including two rows of liquid crystal units arranged parallel to the second incident light.

In addition, please refer to FIG. 4D. FIG. 4D illustrates a schematic diagram of the liquid crystal unit layer 240 including two rows of liquid crystal units 240a~240e arranged parallel to the second incident light $L_I$. As shown in FIG. 4D, the liquid crystal units 240a~240e of the liquid crystal unit layer 240 are parallel arranged in two rows, wherein the liquid crystal units 240a~240c are arranged in the first row and the liquid crystal units 240d~240e are arranged in the second row, but not limited by this case.

Figure 5A:
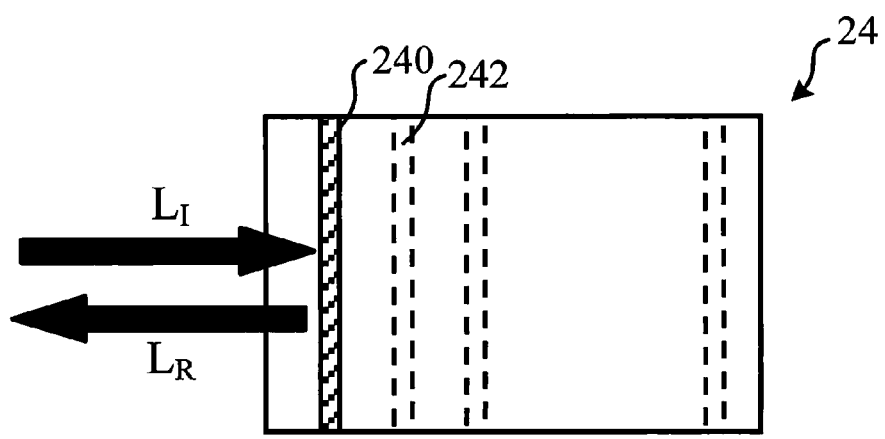
FIG. 5A illustrates a schematic diagram of the optical path difference generating module including multi-layer electro-chromic material.

Please refer to FIG. 5A. FIG. 5A illustrates a schematic diagram of the optical path difference generating module 24 including multi-layer electro-chromic material. As shown in FIG. 5A, if the electro-chromic material 240 is changed to a first color (as the slash in the figure shows), the electro-chromic material 240 will reflect the second incident light $L_I$. Therefore, when the second incident light $L_I$ is emitted to the optical path difference generating module 24, the electro-chromic material 240 showing the first color will reflect the second incident light $L_I$ to generate the second reflected light $L_R$.

Figure 5B:
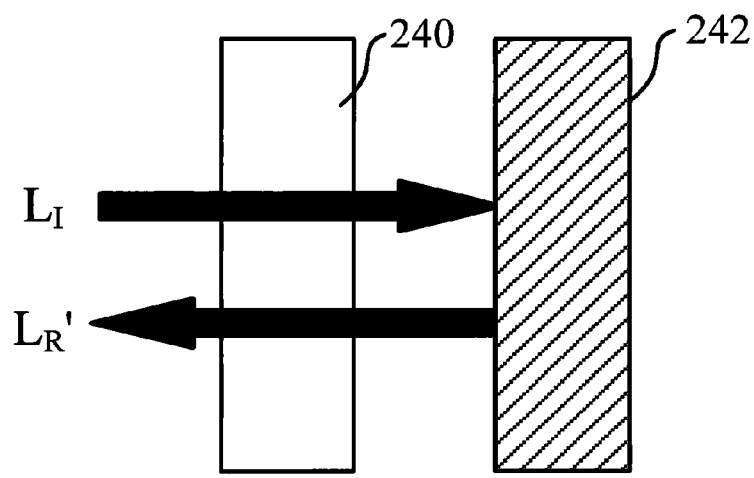
FIG. 5B illustrates a schematic diagram of the second incident light $L_I$ passing through the electro-chromic material 240 but being reflected by the electro-chromic material 242.

FIG. 5B illustrates a schematic diagram of the second incident light $L_I$ passing through the electro-chromic material 240 but being reflected by the electro-chromic material 242. As shown in FIG. 5B, if the electro-chromic material 240 is changed to a second color (as the white color shown in the figure), the second incident light $L_I$ can pass through the electro-chromic material 240. Therefore, when the second incident light $L_I$ is emitted to the optical path difference generating module 24, the second incident light $L_I$ can pass through the electro-chromic material 240 showing the second color, but then the second incident light $L_I$ will be reflected by the electro-chromic material 242 showing the first color to generate the second reflected light $L_R'$.

Comparing FIG. 5A with FIG. 5B, it can be found that the second reflected light $L_R'$ in FIG. 5B is different from the second reflected light $L_R$ in FIG. 5A, so that the optical path difference generating module 24 can change the optical path difference between the first reflected light and the second reflected light by switching the electro-chromic materials 240 and 242 to be the first color or the second color.

Figure 6A:
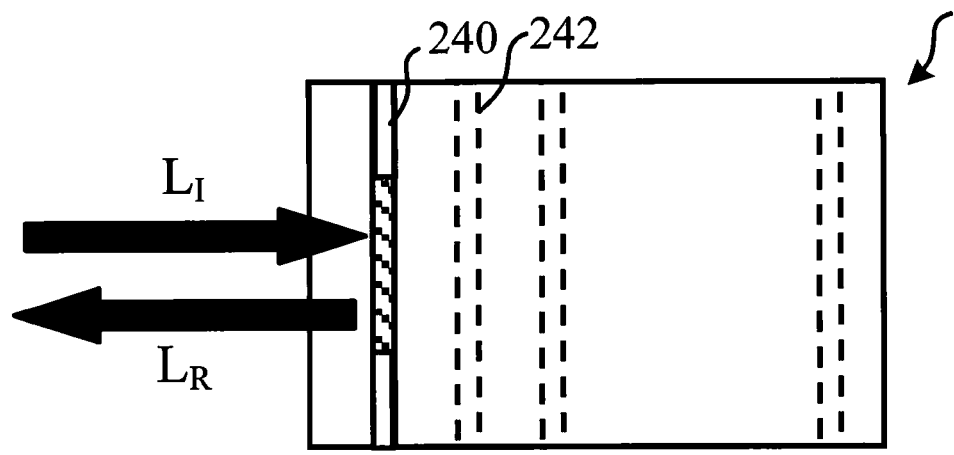
FIG. 6A illustrates a schematic diagram of the optical path difference generating module including multi-layer electro-wetting structure unit.

Please refer to FIG. 6A. FIG. 6A illustrates a schematic diagram of the optical path difference generating module 24 including multi-layer electro-wetting structure unit. As shown in FIG. 6A, if the center of the electro-wetting structure unit 240 is changed to be a first transmission medium (as the slash in the figure shows), the center of the electro-wetting structure unit 240 will reflect the second incident light $L_I$, therefore, when the second incident light $L_I$ is emitted to the optical path difference generating module 24, the electro-wetting structure unit 240 with the first transmission medium will reflect the second incident light $L_I$ to be the second reflected light $L_R$.

Figure 6B:
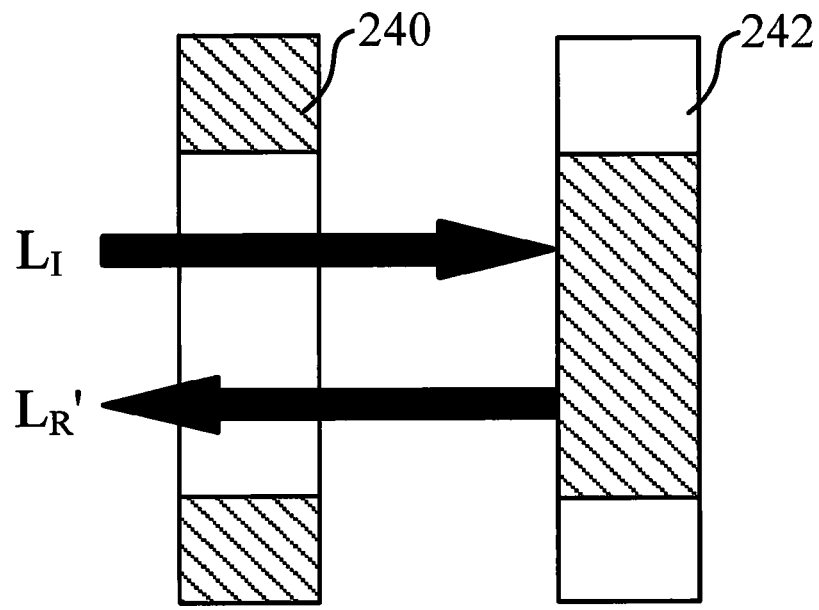
FIG. 6B illustrates a schematic diagram of the second incident light $L_I$ passing through the electro-wetting structure unit 240 but being reflected by the electro-wetting structure unit 242.

FIG. 6B illustrates a schematic diagram of the second incident light $L_I$ passing through the electro-wetting structure unit 240 but being reflected by the electro-wetting structure unit 242. As shown in FIG. 6B, if the electro-wetting structure unit 240 is changed to be a second transmission medium (as the white color shown in the figure), the second incident light $L_I$ can pass through the electro-wetting structure unit 240. Therefore, when the second incident light $L_I$ is emitted to the optical path difference generating module 24, the second incident light $L_I$ will pass through the electro-wetting structure unit 240 with the second transmission medium, but then the second incident light $L_I$ will be reflected by the electro-wetting structure unit 242 with the first transmission medium to be the second reflected light $L_R'$.

Comparing FIG. 6A with FIG. 6B, it can be found that the second reflected light $L_R'$ in FIG. 6B is different from the second reflected light $L_R$ in FIG. 6A, so that the optical path difference generating module 24 can change the optical path difference between the first reflected light and the second reflected light by switching the electro-wetting structure units 240 and 242 to be the first transmission medium or the second transmission medium.

Figure 7A:
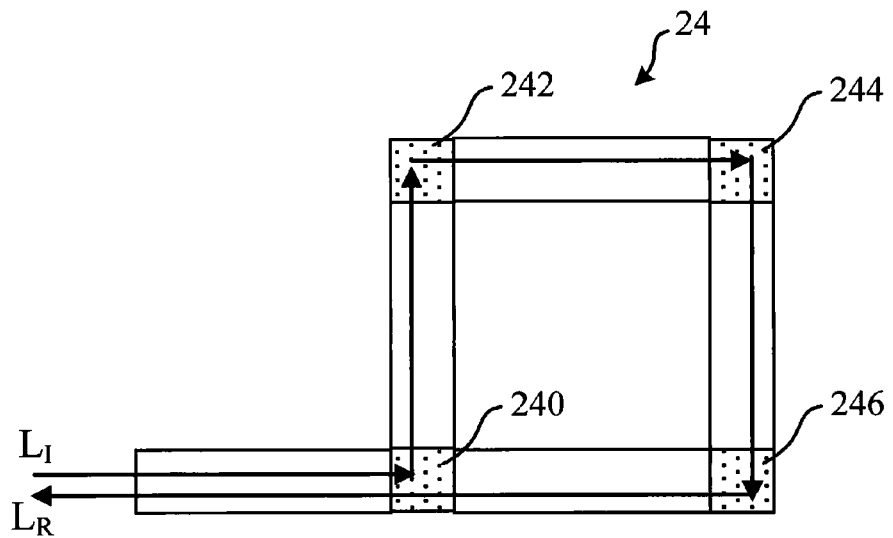
FIG. 7A illustrates a schematic diagram of the optical path difference generating module including a plurality of light switch units.

Please refer to FIG. 7A. FIG. 7A illustrates a schematic diagram of the optical path difference generating module 24 including a plurality of light switch units. In practical applications, the light switch units can be bubble switches or any other switch devices having the refraction angle changing function, there is no specific limitation.

Please refer to FIG. 7A. FIG. 7A illustrates a schematic diagram of the optical path difference generating module 24 including a plurality of light switch units 240, 242, 244, and 246. When the second incident light $L_I$ is emitted to the optical path difference generating module 24, the second incident light $L_I$ will firstly meet the light switch unit 240, since the light switch unit 240 is under the off-state, the second incident light $L_I$ will be refracted by the light switch unit 240 to the light switch unit 242. At this time, since the light switch unit 242 is also under the off-state, the second incident light $L_I$ will be refracted by the light switch unit 242 to the light switch unit 244. Similarly, the second incident light $L_I$ will be further refracted by the light switch unit 244 to the light switch unit 246, and then, the second incident light $L_I$ will be refracted by the light switch unit 246 back to the light switch unit 240. At this time, because the light switch unit 240 is switched to be under the on-state, the second reflected light $L_R$ can be smoothly emitted out of the optical path difference generating module 24.

Figure 7B:
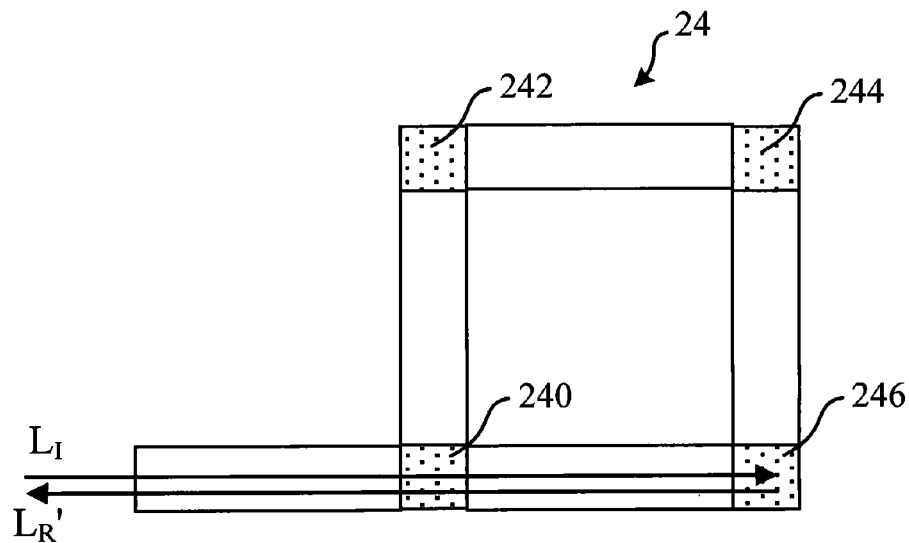
FIG. 7B illustrates a schematic diagram of the plurality of light switch units of the optical path difference generating module generating the second reflected light.

FIG. 7B illustrates a schematic diagram of the plurality of light switch units of the optical path difference generating module 24 generating the second reflected light. As shown in FIG. 7B, when the second incident light $L_I$ is emitted to the optical path difference generating module 24, since the light switch unit 240 is under the on-state, the second incident light $L_I$ can pass through the light switch unit 240 to the light switch unit 246. If the light switch unit 246 has the reflection function, then the light switch unit 246 can reflect the second incident light $L_I$ back to the light switch unit 240. At this time, if the light switch unit 240 is still under the on-state, the second reflected light $L_R'$ can be smoothly emitted out of the optical path difference generating module 24.

A second embodiment of the invention is an OCT apparatus operating method. In this embodiment, the OCT apparatus includes a light source, a light coupling module, and an optical path difference generating module. The optical path difference generating module includes at least one optical device. In fact, the light source can be a coherent light source; the light coupling module can be a light splitter or any other devices having light splitting function, there is no limitation.

Figure 8:
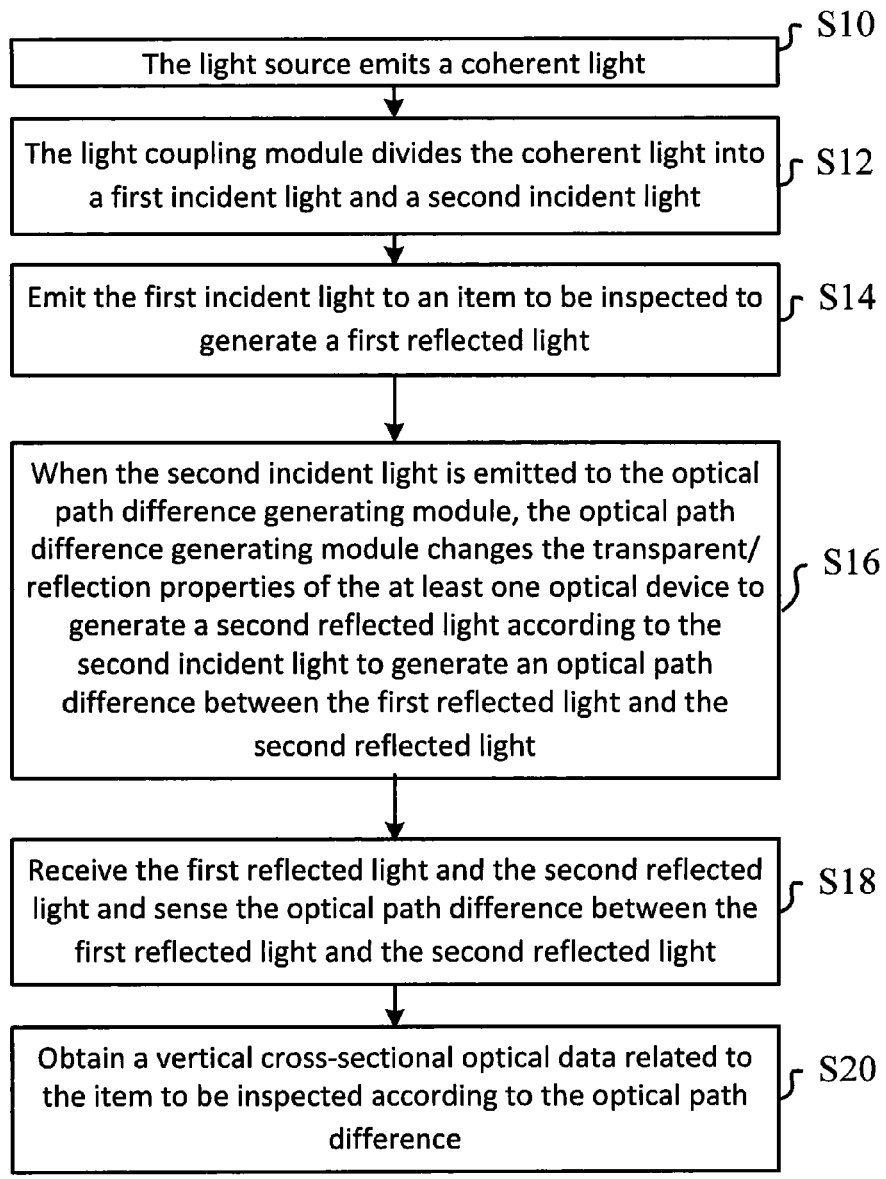
FIG. 8 illustrates a flowchart of the OCT apparatus operating method of the second embodiment in the invention.

Please refer to FIG. 8. FIG. 8 illustrates a flowchart of the OCT apparatus operating method of the second embodiment in the invention. As shown in FIG. 8, at first, in the step S10, the light source emits a coherent light. Then, in the step S12, the light coupling module divides the coherent light into a first incident light and a second incident light. Afterwards, in the step S14, the method emits the first incident light to an item to be inspected to generate a first reflected light. Then, in the step S16, when the second incident light is emitted to the optical path difference generating module, the optical path difference generating module changes the transparent/reflection properties of the at least one optical device to generate a second reflected light according to the second incident light to generate an optical path difference between the first reflected light and the second reflected light.

In an embodiment, the at least one optical device is a plurality of liquid crystal units arranged in a multi-layer form, the optical path difference generating module adjusts rotation angles of the plurality of liquid crystal units to change the transparent/reflection properties of the plurality of liquid crystal units to generate the optical path difference between the second reflected light reflected by the optical path difference generating module and the first reflected light.

In another embodiment, the at least one optical device is a multi-layer electro-chromic material, when the second incident light is emitted to the multi-layer electro-chromic material, the optical path difference generating module will use the multi-layer electro-chromic material to show different transparent/reflection properties corresponding to different color lights of the second incident light to generate the optical path difference between the second reflected light generated by the optical path difference generating module and the first reflected light. It should be noticed that the optical path difference generating module can also provide optical inverting effect according to the relationships between color lights and wavelengths.

In another embodiment, the at least one optical device is a multi-layer electro-wetting structure unit, the second incident light passes through the multi-layer electro-wetting structure unit having different transmission media to generate the optical path difference between the second reflected light generated by the optical path difference generating module and the first reflected light.

In another embodiment, the at least one optical device is a plurality of light guide units, the optical path difference generating module switches the directions of the plurality of light guide units to generate the optical path difference between the second reflected light generated by the optical path difference generating module and the first reflected light.

In another embodiment, the at least one optical device is a plurality of light switch units, for example, the plurality of light switch units can be bubble switches, but not limited by this case. In fact, the optical path difference generating module switches the plurality of light switch units to generate the optical path difference between the second reflected light generated by the optical path difference generating module and the first reflected light.

After the optical path difference between the second reflected light and the first reflected light is generated, in the step S18, the method receives the first reflected light and the second reflected light and senses the optical path difference between the first reflected light and the second reflected light. At last, in the step S20, the method obtains a vertical cross-sectional optical data related to the item to be inspected according to the optical path difference.

Compared to the prior arts, the OCT apparatus and its operating method of the invention is to change the transparent/reflection properties of its optical devices (for example, the liquid crystal unit, the electro-chromic material, the electro-wetting structure unit, the light guide unit, and the light switch unit) to generate an optical path difference, thus, the drawbacks of the conventional OCT apparatus that the complicated optical devices and the shifting/rotating mechanical structure are necessary to generate the optical path difference can be avoided. Therefore, the structure of the OCT apparatus can be largely simplified, and its manufacturing cost can be also reduced, even the effect of changing light frequencies can be provided according to the relationships between the color lights and the wavelengths, so that it has great market potential.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:
1. An optical coherence tomography (OCT) apparatus, comprising:

a light source, for emitting a coherent light;

a light coupling module, for dividing the coherent light into a first incident light and a second incident light, wherein the first incident light is emitted to an item to be inspected and a first reflected light is generated; and an optical path difference generating module comprising at least one optical device, when the second incident light is emitted to the optical path difference generating module, the optical path difference generating module changing the transparent/reflection properties of the at least one optical device to generate a second reflected light according to the second incident light to generate an optical path difference between the first reflected light and the second reflected light;

wherein the at least one optical device is a plurality of light switch units including a first bubble switch, a second bubble switch, a third bubble switch, and a fourth bubble switch; when the optical path difference generating module is operated in a first mode, the second incident light emitted to the optical path difference generating module will firstly met the first bubble switch in the off-state, the first bubble switch in the off-state will refract the second incident light to the second bubble switch in the off-state, and the second bubble switch in the off-state will refract the second incident light to the third bubble switch in the off-state, and the third bubble switch in the off-state will refract the second incident light to the fourth bubble switch in the off-state, and the fourth bubble switch in the off-state will refract the second incident light to the first bubble switch in the on-state, and the second reflected light will pass through the first bubble switch in the on-state out of the optical path difference generating module to form a first mode second reflected light; when the optical path difference generating module is operated in a second mode, the second incident light emitted to the optical path difference generating module will firstly meet the first bubble switch in the on-state and pass through the first bubble switch in the on-state to the fourth bubble switch in the off-state, and the fourth bubble switch in the off-state will refract the second incident light back to the first bubble switch in the on-state and the second reflected light will pass through the first bubble switch in the on-state out of the optical path difference generating module to form a second mode second reflected light; a first optical path difference between the first reflected light and the first mode second reflected light when the optical path difference generating module is operated in the first mode is different from a second optical path difference between the first reflected light and the second mode second reflected light when the optical path difference generating module is operated in the second mode.

2. The optical coherence tomography apparatus of claim 1, wherein the at least one optical device is a plurality of light guide units, the optical path difference generating module switches the directions of the plurality of light guide units to generate the optical path difference between the second reflected light generated by the optical path difference generating module and the first reflected light.

3. The optical coherence tomography apparatus of claim 1, wherein the light coupling module is a light splitter.

4. The optical coherence tomography apparatus of claim 1, further comprising:

a light sensing module, for receiving the first reflected light and the second reflected light and sensing the optical path difference between the first reflected light and the second reflected light; and a processing module, coupled to the light sensing module, for obtaining a vertical cross-sectional optical data related to the item to be inspected according to the optical path difference.

5. A method of operating an optical coherence tomography apparatus, the optical coherence tomography apparatus comprising a light source, a light coupling module, and an optical path difference generating module, the optical path difference generating module comprising at least one optical device, the method comprising the steps of:

(a) emitting a coherent light from the light source;

(b) dividing the coherent light into a first incident light and a second incident light using the light coupling module;

(c) emitting the first incident light to an item to be inspected to generate a first reflected light; and (d) when the second incident light is emitted to the optical path difference generating module, the optical path difference generating module changing the transparent/reflection properties of the at least one optical device to generate a second reflected light according to the second incident light to generate an optical path difference between the first reflected light and the second reflected light;

wherein the at least one optical device is a plurality of light switch units including a first bubble switch, a second bubble switch, a third bubble switch, and a fourth bubble switch; when the optical path difference generating module is operated in a first mode, the second incident light emitted to the optical path difference generating module will firstly meet the first bubble switch in the off-state, the first bubble switch in the off-state will refract the second incident light to the second bubble switch in the off-state, and the second bubble switch in the off-state will refract the second incident light to the third bubble switch in the off-state, and the third bubble switch in the off-state will refract the second incident light to the fourth bubble switch in the off-state, and the fourth bubble switch in the off-state will refract the second incident light to the first bubble switch in the on-state, and the second reflected light will pass through the first bubble switch in the on-state out of the optical path difference generating module to form a first mode second reflected light; when the optical path difference generatiing module is operated in a second mode, the second incident light emitted to the optical path difference generating module will firstly meet the first bubble switch in the on-state and pass through the first bubble switch in the on-state to the fourth bubble switch in the off-state, and the fourth bubble switch in the off-state will refract the second incident light back to the first bubble switch in the on-state and the second reflected light will pass through the first bubble switch in the on-state out of the optical path difference generating module to form a second mode second reflected light; a first optical path difference between the first reflected light and the first mode second reflected light when the optical path difference generating module is operated in the first mode is different from a second optical path difference between the first reflected light and the second mode second reflected light when the optical path difference generating module is operated in the second mode.

6. The method of claim 5, wherein the at least one optical device is a plurality of light guide units, the optical path difference generating module switches the directions of the plurality of light guide units to generate the optical path difference between the second reflected light generated by the optical path difference generating module and the first reflected light.

7. The method of claim 5, wherein the light coupling module is a light splitter.

8. The method of claim 5, further comprising the steps of:
   (e) receiving the first reflected light and the second reflected light and sensing the optical path difference between the first reflected light and the second reflected light; and
   (f) obtaining a vertical cross-sectional optical data related to the item to be inspected according to the optical path difference.

* * * * *